United States Patent [19]

Görlitz et al.

[11] 4,132,692
[45] Jan. 2, 1979

[54] AQUEOUS COATING AGENT FOR STOVING BASED ON AQUEOUS DISPERSION OF EPOXIDE RESIN MIXTURES AND EPOXIDE CURING AGENTS, PROCESS FOR THE MANUFACTURE THEREOF AND THE USE THEREOF

[75] Inventors: Wolf-Dieter Görlitz, Hamburg; Bernhard Broecker, Kelkheim, both of Fed. Rep. of Germany

[73] Assignee: Hoechst Aktiengesellschaft, Fed. Rep. of Germany

[21] Appl. No.: 760,359

[22] Filed: Jan. 19, 1977

[30] Foreign Application Priority Data

Jan. 22, 1976 [DE] Fed. Rep. of Germany ....... 2602255

[51] Int. Cl.$^2$ .............................................. C08L 63/00
[52] U.S. Cl. ........................ 260/29.2 EP; 260/18 EP; 260/29.3; 260/29.4 R; 428/418; 428/460
[58] Field of Search ............... 260/29.3, 29.2 EP, 831, 260/834, 95 R, 29.4 R

[56] References Cited

U.S. PATENT DOCUMENTS 3,449,281   6/1969   Sullivan et al. .................... 260/29.3

Primary Examiner—Theodore E. Pertilla
Attorney, Agent, or Firm—Gordon W. Hueschen

[57] ABSTRACT

The subject of the invention is an aqueous coating agent for stoving, based on aqueous dispersions of epoxide resin mixtures, epoxide resin curing agents and optionally pigments and other customary additives.

2 Claims, No Drawings

AQUEOUS COATING AGENT FOR STOVING BASED ON AQUEOUS DISPERSION OF EPOXIDE RESIN MIXTURES AND EPOXIDE CURING AGENTS, PROCESS FOR THE MANUFACTURE THEREOF AND THE USE THEREOF

BACKGROUND OF THE INVENTION

1. Field of the Invention

In the field of paint resins and coatings the use of polyglycidyl ethers has proved successful owing to their outstanding technological properties. Particular areas of application have been opened up, especially also in the field of coatings, by the use of higher-molecular polyglycidyl ethers having softening points between 50 and 125° C and epoxide equivalents between 440 and 6,000. The epoxide resins, which, in the coatings field, are available either in the form of powders or of solutions in organic solvents, can be crosslinked by means of carboxylic acid anhydrides or by means of dicyandiamide, when it is predominantly the epoxide groups of the polyglycidyl ether which react; it, however, also possible, above all in the case of epoxide equivalents exceeding 2,000, to crosslink them under hot conditions, to give cured coatings, by means of phenolic or melamine resins which are present in a mixture with the polyglycidyl ether to the extent of 10–60%, preferably 20–40%, in which case predominantly the OH groups present in the higher-molecular polyglycidyl ether react. Such systems of the type just mentioned are used above all in the field of container coatings.

Beside the indisputable advantages of powder coatings, a disadvantage which must be mentioned is, above all, their poor levelling which, even using the widely known levelling auxiliaries, cannot be improved to such an extent that the surface of the film is equal in quality to the surface which can be achieved with lacquer films made from systems containing solvents. Further disadvantages are the high investment costs of equipment for powder production and for powder coatings, and the poor flexibility in the choice of layer thicknesses; layer thicknesses below 70–75 $\mu$m can hardly be achieved.

For these and other reasons, coating by means of systems containing solvents will remain indispensable for many areas of application. However, the disadvantages of the heavy pollution of the environment, caused by solvents which evaporate, become increasingly more serious and the construction, which is usually necessary, of expensive plants for final combustion and the effective loss of the solvent represent decisive points in a cost analysis. The use of systems containing solvents is completely ruled out in many cases for reasons of occupational health.

It was, therefore, the object of the present invention to provide aqueous coating agents for stoving, based on aqueous dispersions of epoxide resin mixtures and epoxide resin curing agents, and optionally pigments and other customary additives, the properties of these coating agents being adaptable to the most diverse practical purposes.

It was a further object of the present invention to provide aqueous coating agents for stoving, based on aqueous dispersions of epoxide resin mixtures, in the form of a solvent-free, aqueous, stable dispersion, optionally conjointly with cross-linking agents and other additives required for a particular application, for example agents for improving elasticity, in which coating agents the aliphatic OH groups and/or the epoxide groups should be available for crosslinking.

2. Prior Art

Although it has hitherto been possible to manufacture dispersions of various polymers in water, dispersions of this type have proved very unstable. Settling out has taken place within a short interval of time of a few hours to a few days. The polymer dispersions hitherto known also have poor film-forming properties, which are mainly due to the large particle sizes of the resin, which have hitherto been of the order of magnitude of 50 $\mu$m and higher.

DT-OS No. 1,921,198 describes dispersions, and processes for their manufacture, the resin phase of which can also consist of epoxide resin. In that specification a dispersion which contains particles of an average diameter of 1–5 $\mu$m is manufactured with the aid of a colloid mill, using quaternary ammonium salts as cationic extraneous emulsifiers. Apart from the fact that the process is expensive owing to the use of a colloid mill, the diameter of the particles is still very large.

Processes for the manufacture of stable aqueous epoxide resin emulsions which are completely free from solvent are also known, for example, from DT-OS No. 2,332,165. In that specification, however, a liquid epoxide resin which can be emulsified by means of non-ionic emulsifiers is used as the resin phase. However, owing to their low degree of condensation, liquid epoxide resins are not suitable for many applications; the use of nonionic emulsifiers is not successful with polyglycidyl ethers of a higher degree of condensation, especially with those which are solid at room temperature.

It is stated in U.S. Pat. No. 3,707,526 that water-soluble coating materials can be manufactured by reacting customary, water-insoluble epoxide compounds, such as, for example, diglycidyl ethers of bisphenol A, with dimethylolpropionic acid, optionally in the presence of other carboxlic acids.

The process leaves something to be desired, since the reactants must be heated for several hours in order to manufacture the product, which is then subsequently reacted with amines, such as, for example, alkanolamines, which render it water-soluble. The prolonged time of heating, which is required for the manufacture of the product mentioned above, is not only inappropriate for a commercial process, but is undesirable for other reasons, since it enables a spontaneous, exothermic polymerisation of the epoxide compound to take place, whereby an infusible, insoluble and crosslinked plastic is obtained, which cannot be used as a coating material. In addition, a large molar excess of acid relative to epoxide groups is employed (epoxide groups:acid = 1:2—3), which is undesirable.

U.S. Pat. No. 3,336,253 discloses resins which can be rendered soluble in water and which are reaction products from monoalkanolamines or dialkanolamines and various water-insoluble polymers, in particular epoxide polymers, which contain terminal groups which are reactive towards amines. The resulting products become water soluble by the subsequent neutralisation of the alkanolamine radical with an acid. The preferred reaction products contain one epoxide radical per molecule and are applied as coatings to various substrates. The coatings are subsequently crosslinked by self-polymerisation. One disadvantage of these coating materials is the presence of epoxide radicals, which, in the presence of traces of acid or basic materials, such as, for example, the alkanolamine radicals which are present at one end of each molecule, can undergo a self-polymerisation, crosslinked infusible materials being obtained. As a result of this the stability in storage of the coating compositions is greatly reduced. In the above-mentioned U.S. Pat. No. 3,336,253 it is stated that the stability in storage of the epoxide/alkanolamine reaction products can be increased by removing all unreacted epoxide groups, using various compounds, such as, for example, dialkanolamines. This procedure is undesirable since, in the course thereof, all the reactive sites for subsequent crosslinking, which are necessary for the manufacture of a durable, solventfree coating, are removed. In addition, these products can only be manufactured if very large quantities of dialkanolamines are employed (for example up to 28% of diethanolamine is used in the said U.S. Pat. No. 3,336,253). The resulting coatings are so unstable towards aqueous media that they are completely unserviceable for many purposes. The products manufactured according to DT-OS No. 2,415,100 also contain stoichiometric quantities of alkanolamines, relative to epoxide resin. Although the quantities of amine are reduced to approximately 5% in DT-OS No. 2,426,996, the dispersions still contain considerable quantities of solvent. The process mentioned is also not suitable for manufacturing solvent-free dispersions. Epoxide resin derivatives having the formula I or I', which are used in the present invention, are, however, not described in the literature discussed above.

SUMMARY

The subject of the invention is an aqueous coating agent for stoving, based on aquoeus dispersions of epoxide resin mixtures, epoxide resin curing agents and optionally pigments and other customary additives, characterised in that the aqueous dispersion of epoxide resin mixtures contains, as the binder, (a) an epoxide resin mixture consisting of epoxide resins of the formula I

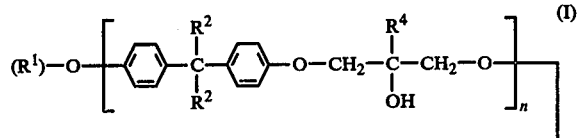

wherein $R^1$ denotes the radical

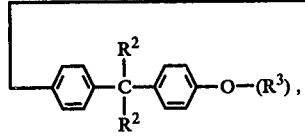

$R^2$ and $R^4$ denote H and/or $CH_3$ and $R^3$ denotes the radical

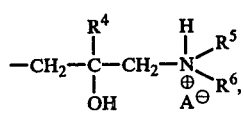

$A^\ominus$ representing the anionic radical of a monocarboxylic acid and $R^5$ and $R^6$ having the following meaning:

| when $R^5$ is the radical given below: | $R^6$ is the radical given below: |
|---|---|
| H | $-CH_2CH_2OH$ |
| H | $-CH_2CH(OH)CH_3$ |
| $-CH_2CH_2OH$ | $-CH_2-CH_2OH$ |
| $-CH_2-CH(OH)CH_3$ | $-CH_2-CH(OH)CH_3$ | and n denotes values from 1.3 to 13; and solid epoxide resins of the formula V

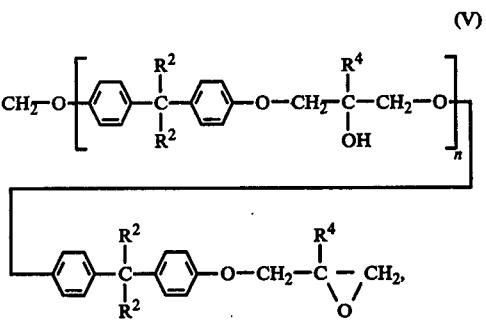

wherein $R^4$ and $R^2$ denote H and/or $CH_3$ and n has a value from 1.3 to 13, the resins having epoxide equivalent weights from 300 to 2,000 and the softening points by the Durrans method being between 50 and 125° C, the mixture of epoxide resins of the formula I and V having the condition that the obtained epoxide resin mixture a' of the formula II

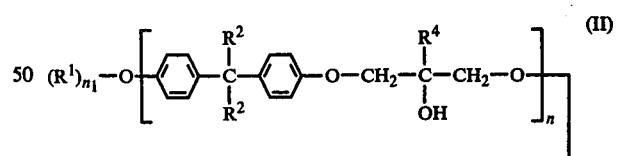

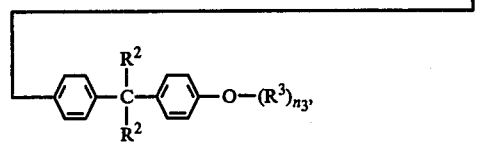

wherein $R^1$, $R^2$, $R^3$, $R^4$, $R^5$, n and $A^\ominus$ have the meaning already mentioned and the sum of $n_1$ and $n_3$ has the value 2 and the ratio of $n_1:n_3$ has values from 20 to 0.1, preferably from 10 to 0.1, and/or (b) an epoxide resin mixture consisting of epoxide resins of the formula I'

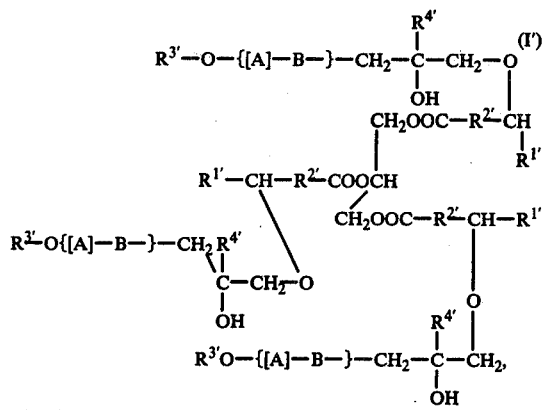

wherein A is the radical

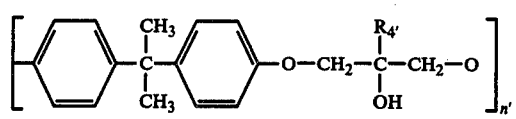

when B represents the radical

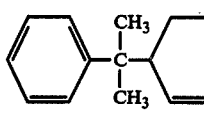

or A is the radical

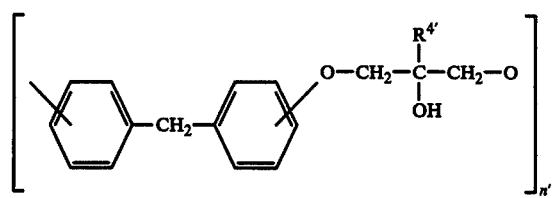

when B represents the radical

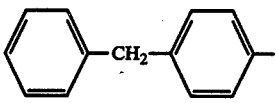

or A represents the radical

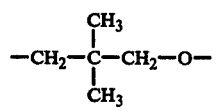

when B has the value zero, or A represents the radical

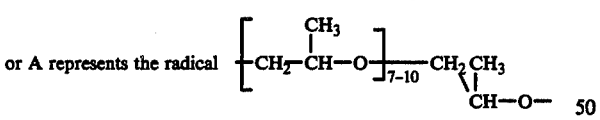

when B has the value zero, and $R^{1'}$ denotes the radical —$(CH_2)_5$-$CH_3$ and $R^{2'}$ denotes the radical —$(CH_2)_7$-CH=CH-$CH_2$—, n' has the value 0 to 13, preferably 0 to 6, $R^{3'}$ denotes the radical

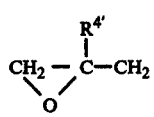

or the radical

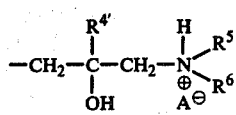

and wherein the last-mentioned grouping is present in at least one radical $R^{3'}$ and $R^5$ and $R^6$ have the following meaning:

| when $R^5$ is the radical given below: | $R^6$ must be the radical given below: |
|---|---|
| H | —$CH_2CH_2OH$ |
| H | —$CH_2CH(OH)CH_3$ |
| —$CH_2CH_2OH$ | —$CH_2$—$CH_2OH$ |
| —$CH_2$—$CH(OH)CH_3$ | —$CH_2$—$CH(OH)CH_3$ | and $A\theta$ represents the anionic radical of a monocarboxylic acid, and epoxide resins of the formula V'

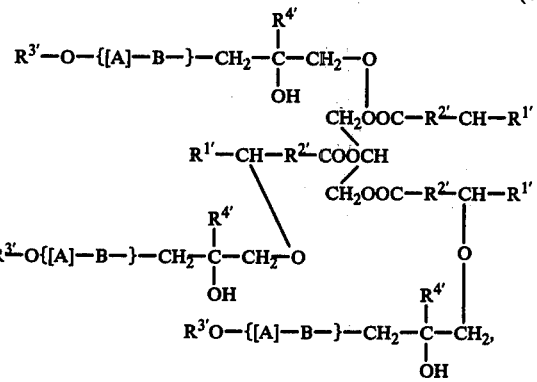

wherein $R^{3'}$ has the meaning

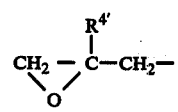

and $R^{1'}$, $R^{2'}$, $R^{4'}$, A, B and n' have the meaning already mentioned and the resins have epoxide equivalent weights of approximately 440 to approximately 4,000, the misture of epoxide resins of the formula I' and V' having the condition that the obtained epoxide resin mixture b' of the formula II'

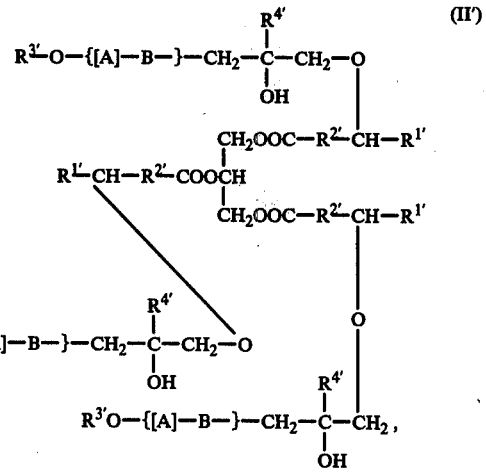

wherein $R^{1'}$, $R^{2'}$, $R^{4'}$, $R^{5'}$, $R^{6'}$, A, B and $A^\theta$ have the meaning already mentioned, wherein $R^{3'}$ denotes the radical

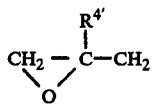

or the radical

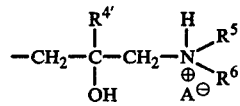

and the last-mentioned grouping is represented by a proportion of at least 10% and at most a proportion of 95%.

A further embodiment of the coating agent of this invention is characterised in that it contains phenolic resols as the epoxide resin curing agents.

A further embodiment of the coating agent of the invention is characterised in that it contains water-soluble melamineformaldehyde condensates as the epoxide resin curing agents.

A further embodiment of the coating agent of the invention is characterised in that it contains diyandiamide as the expoxide resin curing agent.

A preferred embodiment of the coating agent of the invention is characterised in that it contains a combination of phenolic resols and/or water-soluble melamineformaldehyde condensates, together with phosphoric acid, as the epoxide resin curing agent.

A further subject of the invention is a process for the manufacture of the coating agent of this invention, characterised in that a mixture of (a) solid epoxide resins of the general formula V

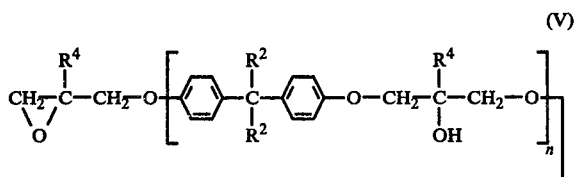

wherein $R^4$ and $R^2$ denote H and/or $CH_3$ and n has a value from 1.3 to 13, the resins have epoxide equivalent weights from 300 to 2,000 and the softening points by the Durrans method are between 50 and 125° C, and (b) epoxide resins of the general formula V'

(V')

—continued

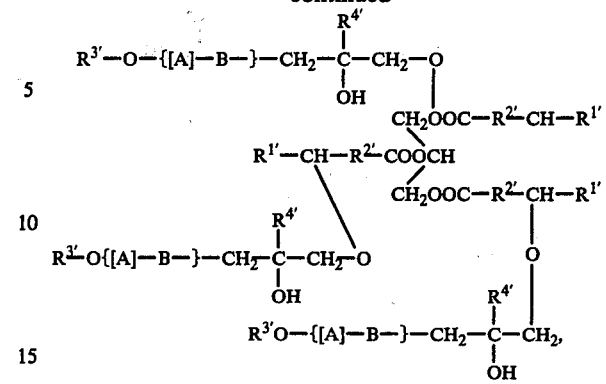

wherein $R^{3'}$ has the meaning

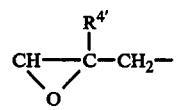

and $R^{1'}$, $R^{2'}$, $R^{4'}$, A, B and n' have the meaning already mentiond and the resins have epoxide equivalent weights of approximately 440 to approximately 6,000, is reacted, at 50 to 170° C, whilst stirring well, with 0.1 to 1.0 mol (relative to 100 g of epoxide resin mixture (a and b) of an alkanolamine or dialkanolamine having the formula VI

 (VI)

wherein $R^5$ and $R^6$ have the meaning already mentioned, in the presence of at least one inert organic solvent having a boiling point between 50 and 170° C, and 0.01 to 1.0 mol of a monocarboxylic acid (relative to 100 g of epoxide resin mixture (a and b) having a pKa value of 2 to 5 is added to the resulting reaction product, it being necessary that the equivalent ratio of monocarboxylic acid to alkanolamine or dialkanolamine is 0.7:1 to 3:1, and the required quantity of water is added to the mixture whilst mixing vigorously at 20 to 70° C and the organic solvent present in the dispersion is removed by azeotropic distillation with water in vacuo at 30 to 60° C, the epoxide resin curing agents and optionally the pigments and the other customary additives being added to the reaction batch before, during or after the reaction.

Epoxide resins having the formula I wherein the anionic radical consists of a polyhydroxymonocarboxylic acid, have been described by the same applicant in the German patent application of the same date entitled: "Epoxide resin, process for the manufacture thereof and the use therof" (file reference P 26 02 227.5) Epoxide resins having the formula I wherein the anionic radical consists of a monocarboxylic acid, have been described by the same applicant in the German patent application of the same date entitled: "Solid epoxide resin soltuion which is self-emulsifiable with water, process for the manufacture thereof and the use thereof" (file reference P 26 02 221.9). Epoxide resins having the formula I' have been descirbed by the same applicant in the German patent application of the same data entitled: "Epoxide resin derivatives, process for the manufacture thereof and the use thereof" (file reference P 26 02 222.0). Mixtures of epoxide resins having the formula I and I' have been described by the same applicant in the German patent application of the same date entitled: "Mixture of solid solutions of epoxide resins which is self-emulsifiable with water — process for the manufacture thereof and the use thereof" (file reference P 26 02 220.8).

The use of phenolic resols as epoxide resin curing agents is known and is described, for example, in the book: "Epoxydverbindungen und Epoxydharze" ("Epoxide Compounds and Epoxide Resins") by Dr. Alred Max Paquin, Springer Verlag, Berlin/Göttingen/Heidelbert (1958), on pages 517 to 520.

Phenolic resols which can be used as epoxide resin curing agents are those having the general structural unit according to formula III

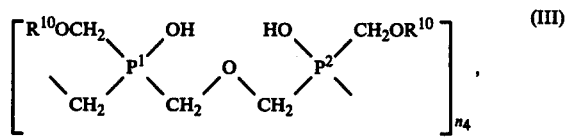

wherein $n_4$ has values from 2 to 15 and $P^1$ and $P^2$ denote the radical

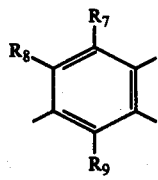

and/or the radical

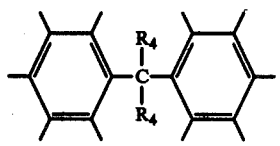

and $R^{10}$ denots H and/or an unsubstituted, organic aliphatic radical having 1 to 4 carbon atoms, wherein $R_7$, $R_8$ and $R_9$ denote hydrogen and/or an unsubstituted organic aliphatic or cycloaliphatic radical having 1 to 12 carbon atoms or an unsubstituted, organic aromatic or araliphatic radical having 1 – 12 carbon atoms.

The phenolic resols are present in quantities of 10 to 40 percent by weight, preferably 20 to 30 percent by weight, relative to the total solids content of the coating agent.

The reaction product of 2,2-bis-[4-hydroxyphenyl]-propane with formaldehyde in a molar reaction ratio of 1:4 to 1:6, which has been etherified with n-butanol is used most preferentially as the phenolic resol.

The curing of epoxide resins by means of aminoplasts is described in the book: "Epoxydverbindungen und Epoxydharze" ("Epoxide Compounds and Epoxide Resins") by Dr. Alfred Max Paquin, Springer Verlag, Berlin/Göttinger/Heidelberg (1958), on pages 381 to 388 and 520 to 522. The coating agent preferably contains a melamine resin of the general formula IV

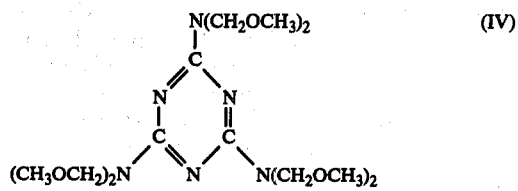

as the water-soluble melamine-formaldehyde condensation product. The water-soluble melamine-formaldehyde condensation products are present in quantities of 10 to 40 percent by weight, preferably 20 to 30 percent by weight, relative to the weight of total solids in the coating agent.

Together with the phenolic resols and/or water-soluble melamine-formaldehyde products, the coating agent of the invention preferably contains phosphoric acid as a curing catalyst. It is customary to use 5 to 15 percent by weight, relative to the weight of solids in the coating agent, of an aqueous 5 to 10% strength by weight phosphoric acid.

It is also possible to use dicyandiamide as the curing agent, 3 to 4 percent by weight, relative to the weight of the total solids, usually being present.

The coating agent can be manufactured by the process already described above, the epoxide resin curing agents and the other desired additives being added to the reaction batch before, during or after the reaction.

The phenolic resol can be added to the reaction batch after the completion of the reaction with the added dialkanolamine. For this, the phenolic resol, dissolved in an organic solvent which is compatible with the solvent and the reaction batch, is added, whilst stirring well, in the course of 10 to 180 minutes, preferably 15 to 45 minutes, at 30 to 90° C, preferably at 60 to 80° C. The phenolic resol is preferably added in solution in an organic solvent which is already present in the reaction batch. The further manufacture of the coating agent is then carried out as already described.

It is, however, also possible to manufacture the coating agent from expoxide resin dispersions which are in stock by mechanical mixing with the other ingredients required. If a phenolic resol is included in the ingredients required, the phenolic resol is added in a state in which it is dissolved or dispersed in water when it is mixed with the eoxide resin dispersions. If a water-soluble melamine-formaldehyde condensation product is to be incorporated into the coating agent, it is incorporated in the form of an aqueous solution, by stirring well. The epoxide resin dispersions which are in stock can be mixed at room temperature with the other ingredients required. The manufacture of phenolic resols dispersed in water is described, for example, in DT-OS No. 2,330,849.

In some cases it can be desirable that the phenolic resol which is contained in the coating agent is partially or wholly linked to the eoxide resin in the form of an adduct or in the form of a pre-condensate. The reactions which are possible in the formation of an adduct or in the pre-condensation have been discussed in the book by Paquin already quoted, on page 518. In the actual operation of the process described, the phenolic resol is added under hot conditions, at the temperatures already indicated, to the reaction batch after the reaction with the dialkanolamine is complete and stirring within the indicated temperature range is then continued until the desired formation of adduct or precondensation has taken place in the reaction to an adequate extent, to give a rise in viscosity. In carrying out the process in practice, it is therefore possible to discontinue the formation of adduct or pre-condensation in the reaction solution as soon as the reaction solution has the desired viscosity.

The coating agent of the present invention can contain, as a levelling auxiliary, siloxane-glycol copolymers which are in themselves known, in quantities of 0.5 to 6%, preferably 1 to 4% by weight, relative to the solids content of the coating agent. Siloxaneglycol copolymers which should be mentioned as suitable for use as levelling auxiliaries are those described in the literature by Messrs. Dow Corning, for example "Dow Corning F-11,574" or "DC 193-silicone oil" or "DC 195-silicone oil" (see the company's leaflets 90-153-01, November 1970 or CP-193-G-R(o), February 1967).

An example of further levelling auxiliaries from the category of the alkinediols which should be mentioned is the levelling auxiliary of the formula VII

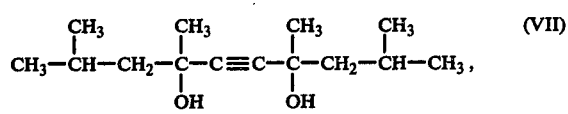

such as has been descirbed by Messrs. W. Biesterfeld & Co. in the literature under the designation "Surfynol 104" (or Surfynol 104 A, 104 E or 104 H, if Type 104 is present in a dissolved form in various solvents) (see technical leaflet of Messrs. W. Biesterfeld & Co.) or there are also alkinediols of varying degrees of oxalkylation, such as, for example, those of the formula VIII

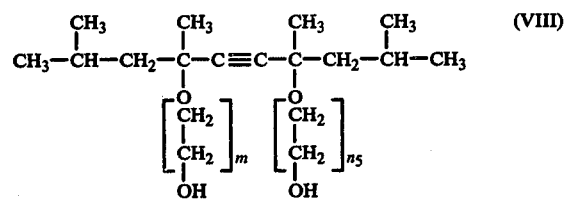

which has $m + n_5 = N = 3.5$, "Surfynol 465" which has $m + n_5 = N = 10$ and "Surfynol 485" which has $m + n_5 = N = 30$, such as have been descirbed by Messrs. W. Biesterfeld & Co. in their technical leaflet under the designations "Surfynol 440."

The coating agent can also contain wetting agents and antifoaming agents, for example in the form of alkinediols, in quantities of 0.1 to 3, preferably 0.5 to 1, % by weight, relative to the weight of the solids in the coating agent. The aqueous coating agent according to the invention can be used for coating metals, for example for lacquering containers and lacquering tin cans, the coating agent being applied to the sheet metal by spraying, rolling or other processes. After exposure to air at room temperature, the coatings are stoved at temperatures between 160 to 220° C, preferably at 180 to 200° C, for 5 to 20 minutes, preferably 8 - 12 minutes. The stoved coatings which are obtained are distinguished by giving coatings which are resistant to water and diluted organic acids in sterlisation, are suitable for deep-drawing and leave good adhesion.

The invention is illustrated by means of the following examples:

EXAMPLE 1

300 g of an epoxide resin of the general formula V wherein n has a value of 9.7 to 13.0, having a softening point of 118° C by the Durrans method and an epoxide equivalent weight of 1,865 (an expoide resin of this type is described by Hoechst AG under the designation EP 307 in the selling range technical leaflets "Epoxidharze" ("Epoxide Resins")) were melted at a temperature rising to approx. 130° C and 75 g of an epoxide resin of the formula V' according to DT-AS No. 2,132,683, Example 1, which had been improved in elasticity and which had an epoxide equivalent weight of 470 (an epoxide resin of Hoechst AG designated EP 151, see selling range technical leaflets "Epoxidharze" ("Epoxide Resins") was used) were added. 60 g. of toluene and 90 g of n-butanol were added to the melt at 130° C in the course of one hour, and the temperature fell gradually to 80° C. 18 g (0.046 mol/100 g of EP resin) of diethanolamine were then added in the course of 15 minutes. The mixture was left to react further for one hour at 80° C. 180 g of phenolic resol (prepared from: 2,2-bis[4-hydroxyphenyl]-propane resol, etherified with n-butanol, charge ratio 1 : 4, condensation reaction carried out for 4 days at 25° C; catalyst: NaOH; neutralised with HCl; acidified with $H_3PO_4$; degree of ehterification: 35 parts, viscosity at 25° C of a 60% strength solution in n-butanol equals 215; see technical data sheet of Hoechst AG "Nichtplastifizierte Phenolharze,1974" ("Unplasticised Phenolic Resins, 1974"), dissolved to form a 70& strength solution in n-butanol, were then added in the course of 15 minutes. 21.7 g of 90% strength latic acid were now added at 70° C in the course of one hour. A solution is obtained, the epoxide resin component of which contains the not reacted epoxide resins of the formula V and V' and the reaction products of the epoxide resins of the formula V and V' with diethanolamine and lactic acid, the reaction products corresponding to the epoxide resins of the formula I and I'. The quantitative composition is to be best explained by the formulas II and II'.

The mixture was cooled to 40° C and 750 g of distilled water were stirred in in the course of one hour. Finally, the solvent mixture was removed by azeotropic distillation with water in vacuo at 40° C. The resulting dispersion was filtered through a 56 μ gauze.

Characteristic values: Solids content 45.1%
Viscosity
at 25° C: 48 mPas (Brookfield, Spindel 2/60 U
pH value: 4.3.

The composition of the resin component of the dispersion is represented to the extent of 60% by formula II, 15% by formula II' and 25% by a phenol resol of formula III as an epoxide resin curing agent, wherein, for the constituent according to formula II, $R^1$ and $R^3$ have the same meaning as in formula II, $R^2$ and $R^4$ denote H, $R^5$ and $R^6$ denote the radical —$CH_2$-$CH_2OH$, $A\ominus$ denotes the radical $CH_3$-$CH(OH)COOa$, n has a value from 9.7 to 13.0 and $n_1$; $n_3$ has a value from 0.2 to 0.5 and, for the constituent according to formula II', 83% of the radicals $R^{3'}$ have the meaning

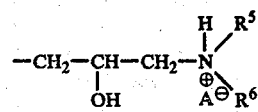

and 17% of the radicals $R^{3'}$ have the meaning

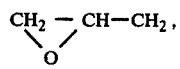

$R^{1'}, R^{2'}, R^{4'}, R^5, R^6$, A, B and $A^{\ominus}$ having the meaning already mentioned and, for the constituent according to formula III, $p^1$ and $p^2$ denote the radical

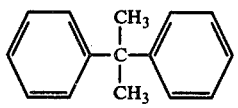

and $R^{10}$ denotes the radical H and/or the radical $CH_3$-$CH_2$-$CH_2$-$CH_2$— and $n_4$ has values from 2 to 15.

The received dispersion was mixed with 10% (relative to the solids content of the dispersion) of a 8.5% strength $H_3PO_4$.

Films approx. 30 μm thick were applied by means of a Handcoater to electrolytic sheet metal and were exposed to the air for 10 minutes. Then they were stoved for 10 minutes at 200° C. A glossy, transparent film of good elasticity and good resistance to sterilisation, even in the presence of organic acids, was obtained.

EXAMPLE 2

300 g of an epoxide resin of the general formula V wherein n has a value of 9.7 to 13.0, having a softening point of 118° C by the Durrans method and an epoxide equivalent weight of 1,865 (an epoxide resin of this type is described by Hoechst AG under the designation EP 307 in the selling range techanical leaflets "Epoxidharze" ("Epoxide Resins")) were melted at a temperature rising to approx. 130° C and 75 g of an epoxide resin of the formula V' according to DT-AS No. 2,132,683, Example 1, which has been improved in elasticity and had an epoxide equivalent weight of 470 (an epoxide resin of this type is described by Hoechst AG under the designation EP 151 in the selling range technical leaflets "Epoxidharze" ("Epoxide Resins")) were added. 60 g of toluene and 90 g of n-butanol were added to the melt at 130° C in the course of 1 hour, and the temperature fell gradually to 80° C. 18 g (0.046 mol/100 g of EP resin) of diethanolamine were then added in the course of 15 minutes. The mixture was left to react further at 80° C for one hour. 180 g of a phenolic resol (as used in Example 1), dissolved to form a 70% strength solution in n-butanol, were then added in the course of 15 minutes. 6.9 g of 98% strength formic acid were now added at 70° C in the course of 1 hour.

A solution is obtained, the epoxide resin component of which contains the not reacted epoxide resins of the formula V and V' and the reaction products of the epoxide resins of the formula V and V' with diethanolamine and formic acid, the reaction products corresponding to the epoxide resins of the formula I and I'. The quantitiative composition is to be best explained by the formula II and II'.

The mixture was cooled to 40° C and 750 g of distilled water were stirred in in the course of one hour. Finally, the solvent mixture was removed by axeotropic distillation with water in vacuo at 40° C. The resulting dispersion was filtered through a 56 μm gauze.

mPas values: Solids content: 46.7% Viscosity at 25° C : 5,800 mPas (Brookfield, Spindle 4/60 U) pH value : 3.35.

The composition of the resin component of the dipersion is represented to the extent of 60% by formula II, 15% by formula II' and 25% by a phenol resol of formula III as an epoxide resin curing agent, wherein, for the constituent according to formula II, $R^1$ and $R^3$ have the same meaning as in formula II, $R^2$ and $R^4$ denote H, $R^5$ and $R^6$ denote the radical —$CH_2$-$CH_2OH$, $A\ominus$ denotes the radical $HCOO\ominus$, n has a value from 9.7 to 13.0 and $n_1$: $n_3$ has a value from 0.2 to 0.5 and, for the constituent, according to formula II' 83% of the radicals have the meaning

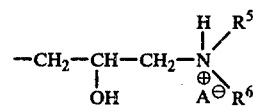

and 17% of the radicals $R^{3'}$ have the meaning

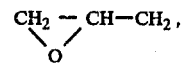

$R^{1'}, R^{2'}, R^{4'}, R^5, R^6$, A, B and $A\ominus$ having the meaning already mentioned and, for the constituent according to formula III, $p^1$ and $P^2$ denote the radical

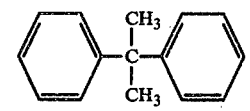

and $R^{10}$ denotes the radical H and/or the radical $CH_3$-$CH_2$-$CH_2$-$CH_2$— and $n_4$ has values from 2 to 15.

The received dispersion was mixed with 10% (relative to the solids content of the dispersion) of a 8.5% strength $H_3PO_4$. By means of the coating agent received in this way films approx. 30 μm thick were applied by means of a Handcoater to electrolytic sheet metal and were exposed to the air for 10 minutes. Then they were stoved for 10 minutes at 200° C. A glossy, transparent film of good elasticity and good resistance to sterilisation, even in the presence of organic acids, was obtained.

EXAMPLE 3

300 g of an epoxide resin of the general formula V wherein n has a value of 9.7 to 13.0, having a softening point of 118° C by the Durrans method and an epoxide equivalent weight of 1,865 (an epoxide resin of this type is described by Hoechst AG under the designation EP 307 in the selling range technical leaflets "Epoxidharze" ("Epoxide Resins"))were melted at a temperature rising to approx. 130° C and 75 g of an epoxide resin of the formula V' according to DT-AS No. 2,132,683, Example 1, which had been improved in elasticity and had an epoxide equivalent weight of 470 (an epoxide resin of this type is described by Hoechst AG under the designation EP 151 in the selling range technical leaflets "Epoxidharze" ("Epoxide Resins")) were added. 150 g of n-butanol were added to the melt at 130° C in the course of 1 hour, and the temperature fell gradually to 80° C. 10.8 g (0.028 mol/100 g of EP resin) of diethanolamine were then added in the course of 15 minutes. The mixture was left to react further at 80° C for 1 hour. 180 g of a phenolic resol (which is indicated in Example 1), dissolved to form a 70% strength solution in n-butanol, were then added in the course of 15 minutes. 51 g of 50% strength gluconic acid were now added at 70° C in the course of one hour.

A solution is obtained, the epoxide resin component of which contains the not reacted epoxide resins of the formula V and V' and the reaction products of the epoxide resins of the formula V and V' with diethanolamine and gluconic acid, the reaction products corresponding to the epoxide resins of the formula I and I'. The quantitative composition is to be best explained by the formula II and II'.

The mixture was cooled to 40° C and 750 g of distilled water were stirred in in the course of one hour. After the addition of water had been completed, 5 g of a levelling auxiliary (according to formula VII) (see technical data sheet of Messrs. Biesterfeld & Co.) were added. Finally, the n-butanol was removed by azeotropic distillation with water in vacuo at 40° C. After the n-butanol had been removed by distillation (as described in Example 1),5.0 g of silicone oil based on a siloxane-glycol copolymer having the designation DC 195 (see technical data sheet of Messrs. Dow Corning) were stirred in thoroughly. The resulting dispersion was filtered through a 56 μm gauze.

Characteristic values: Solids content: 53.0% Viscosity at 25° C : 6,000 mPas (Brookfield, Spindle 4/60 U) pH value : 4.5.

The composition of the resin component of the dispersion is represented to the extent of 80% by formula II, 15% by formula II' and 25% by a phenol resol of the formula III, wherein, for the constituent according to formula II, $R^1$ and $R^3$ have the same meaning as in formula II, $R^2$ and $R^4$ denote H, $R^5$ and $R^6$ denote the radical $-CH_2-CH_2OH$, $A^\ominus$ denotes the radical $HOCH_2-[CH(OH)]_4COO^\ominus$, n has a value from 9.7 to 13.0 and $n_1 : n_3$ has a value from 1.2 to 1.5, and, for the constituent according to formula II', approx. 57% of the radicals $R^{3'}$ have the meaning

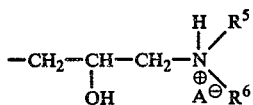

and approx. 43% of the radicals $R^{3'}$ have the meaning

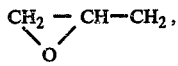

$R^{1'}$, $R^{2'}$, $R^{4'}$, $R^5$, $R^6$, A, B and $A^\ominus$ having the meaning already mentioned and, for the constituent according to formula III, $P^1$ and $P^2$ denote the radical.

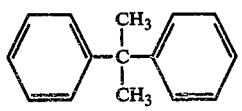

and $R^{10}$ denotes the radical H and/or the radical $CH_3$-$CH_2$-$CH_2$-$CH_2$— and $n_4$ has a value from 2 to 15.

The received dispersion was mixed with 10% (relative to the solids content of the dispersion) of a 8.5% strength $H_3PO_4$. By means of the coating agent received in this way films approx. 30 μm thick were applied by means of a Handcoater to electrolytic sheet metal and were exposed to the air for 10 minutes. Then they were stoved for 10 minutes at 200° C. A glossy, transparent film of good elasticity and good resistance to sterilisation, even in the presence of organic acids, was obtained.

EXAMPLE 4

291 g of an epoxide resin of the general formula V, wherein n has a value from 9.7 to 13.0, having a softening point of 118° C by the Durrans method and an epoxide equivalent weight of 1,865 (an epoxide resin of this type is described by Messrs. Hoechst AG under the designation EP 307 in the technical leaflets "Epoxidharze" ("Epoxide Resins")) were melted. 36 g of toluene and 108 g of n-butanol were added at 130° C to the melt in the course of 1 hour, and the temperature fell gradually to 80° C. 9 g (0.03 mol/100 g of EP resin) of diethanolamine were then added in the course of 15 minutes. The mixture was left to react further at 80° C for 1 hour and 23.9 g of 90% strength by weight lactic acid were then added at 70° C in the course of 1 hour.

A solution is obtained, containing the not reacted epoxide resins of the formula V and the reaction product of the formula V with diethanolamine and lactic acid, the reaction product corresponding to the epoxide resin of the formula I. The compositin is to be best explained by the formula II.

The mixture was cooled to 40° C and 450 g of distilled water were stirred in in the course of 1 hour. Finally, the solvent mixture was removed by azeotropic distillation with water in vacuo at 40° C. The resulting dispersion was filtered through a 56 μm gauze.

Characteristic values: Solids content: 42.5% Viscosity at 25° C : 1,800 mPas (Brookfield, Spindle 3/30 U) pH value: 3.25

The composition of the resin component of the dispersion is represented by formula II, wherein $R^1$ and $R_3$ have the same meaning as in formula II, $R^2$ and $R^4$ denote H, $R^5$ and $R^6$ denote the radical $-CH_2-CH_2-OH$, $A^\ominus$ denotes the radical $CH_3-CH(OH)-COO^\ominus$, n has a value from 9.7 to 13.0 and $n_1 : n_3$ has a value from 0.5 to 0.7.

11 g of the received dispersion were well stirred with 1.1% of tylose H 4,000, relative to solids content (hydroxy ethyl cellulose of Messrs. Hoechst AG, with a medium content of $OC_2H_4$ of 35%), further with 3 g of hexamethoxy methylmelamine (described by Messrs. Hoechst AG in technical leaflet as MF 900) and 1 g of 8.5% strength $H_3PO_4$. By means of this coating agent a film 24 μm thick was applied to electrolytic sheet metal by means of a Handcoater and was exposed to the air for 10 minutes and stoved for 10 minutes at 200° C. A glossy, transparent film of good elasticity and good resistance to sterilisation was obtained.

In another embodiment 11.3 g of the received dispersion were well stirred with 0.7% of tylose H 4,0000, relative to solids content, with 3 g of hexamethoxy methylmelamine and 1 g of 8.5% strength of $H_3PO_4$. The film applied and stoved as above mentioned showed elasticity and resistance to sterilisation.

EXAMPLE 5

363.7 g of an epoxide resin of the general formula V wherein n has a value from 5.0 to 5.8, having a softening point of 95° C by the Durrans method and an epoxide equivalent weight of 910 (an epoxide resin of this type is described by Messrs. Hoechst AG under the designation EP 304 in the technical leaflets "Epoxidharze" ("Epoxide Resins")) were melted. 45 g of toluene and 135 g of n-butanol were added at 125° C to the melt in the course of 1 hour, and the temperature fell gradually to 80° C. 4 g (0.01 mol/100 g of EP resin) of diethanolamine were then added in the course of 15 minutes. The mixture was left to react further at 80° C for one hour and 11 g of 50% strength gluconic acid were then added at 70° C in the course of 1 hour. A solution is obtained, containing the not reacted epoxide resins of the formula V and the reaction product of the formula V with diethanolamine and gluconic acid, the reaction product corresponding to the epoxide resin of the formula I. The composition is to be best explained by the formula II.

The mixture was cooled to 40° C and 450 g of distilled water were stirred in in the course of 1 hour. Finally, the solvent mixture was removed by azeotropic distillation with water in vacuo at 40° C. The resulting dispersion was filtered through a 56 μm gauze.

Characteristic values: Solids content: 63.3% Viscosity at 25° C : 1,260 mPas (Brookfield, Spindle 3/30 U) pH value : 3.7

The composition of the resin component of the dispersion is represented by formula II, wherein $R^1$ and $R^3$ have the same meaning as in formula II, $R^2$ and $R^4$ denote H, $R^5$ and $R^6$ denote the radical $-CH_2-CH_2-OH$, $A^\ominus$ denotes the radical $CH_2(OH)[CH(OH)]_4COO^\ominus$, n has a value from 5.0 to 5.8 and $n_1 : n_3$ has a value from 8.8 to 9.2.

11 g of the received dispersion were well stirred with 1.1% of tylose H 4,000, relative to solids content (hydroxy ethyl cellulose of Messrs. Hoechst AG, with a medium content of $OC_2H_4$ of 35%), further with 3 g of hexamethoxy methylmelamine (described by Messrs. Hoechst AG in technical leaflet as MF 900) and 1 g of 8.5% strength $H_3PO_4$. By means of this coating agent a film 24 μm thick was applied to electrolytic sheet metal by means of a Handcoater and was exposed to the air for 10 minutes and stoved for 10 minutes at 200° C. A glossy, transparent film of good elasticity and good resistance to sterilisation was obtained.

EXAMPLE 6

363.7 g of an epoxide resin of the general formula V wherein n has a value from 9.7 to 13.0, having a softening point of 118° C by the Durrans method and an epoxide equivalent weight of 1,865 (an epoxide resin of this type is described by Messrs. Hoechst AG under the designation EP 307 in the technical leaflets "Epoxidharze" ("Epoxide Resins")) were melted. 45 g of toluene and 135 g of n-butanol were added at 125° C to the melt in the course of 1 hour, and the temperature fell gradually to 80° C. 4 g (0.01 mol/100 g of EP resin) of diethanolamine were then added in the course of 15 minutes. The mixture was left to react further at 80° C for 1 hour and 11 g of 50% strength gluconic acid were then added at 70° C in the course of 1 hour. A solution is obtained, containing the not reacted epoxide resins of the formula V and the reaction product of the formula V with diethanolamine and gluconic acid, the reaction product corresponding to the epoxide resin of the formula I. The composition is to be best explained by the formula II. The mixture was cooled to 40° C and 450 g of distilled water were stirred in in the course of 1 hour. Finally, the solvent mixture was removed by azeotropic distillation with water in vacuo at 40° C. The resulting dispersion was filtered through a 56 μm gauze.

Characteristic values: Solids content: 61.7% Viscosity at 25° C : 1,008 mPas (Brookfield, Spindle 3/30 U) pH value : 3.7

The composition of the resin component of the dispersion is represented by formula II, wherein $R^1$ and $R^3$ have the same meaning as in formula II, $R^2$ and $R^4$ denote H, $R^5$ and $R^6$ denote the radical $-CH_2-CH_2-OH$, $A^\ominus$ $CH_2(OH)[CH(OH)]_4COO^\ominus$, n has a value from 9.7 tl 13.0 and $n_1 : n_3$ has a value from 3.6 to 4.0.

11 g of the received dispersion were well stirred with 1.1% of tylose H 4,000, relative to solids content (hydroxy ethyl cellulose of Messrs. Hoechst AG, with a medium content of $OC_2H_4$ of 35%), further with 3 g of hexamethoxy methylmelamine (described by Messrs. Hoechst AG in technical leaflet as MF 900) and 1 g of 8.5% strength $H_3PO_4$. By means of this coating agent a film 24 μm thick was applied to electrolytic sheet metal by means of a Handcoater and was exposed to the air for 10 minutes and stoved for 10 minutes at 200° C. A glossy, transparent film of good elasticity and good resistance to sterilisation was obtained.

EXAMPLE 7

363.7 g of an epoxide resin of the general formula V wherein n has a value from 9.7 to 13.0, having a softening point of 118° C by the Durrans method and an epoxide equivalent weight of 1.865 (an epoxide resin of this type is described by Messrs. Hoechst AG under the designation EP 307 in the technical leaflets "Epoxidharze" ("Epoxide Resins")) were melted. 45 g of toluene and 135 g of n-butanol were added at 125° C to the melt in the course of 1 hour, and the temperature fell gradually to 80° C. 4 g (0.01 mol/100 g of EP resin) of diethanolamine were then added in the course of 15 minutes. The mixture was left to react further at 80° C for 1 hour and 11 g of 50% strength gluconic acid were then added at 70° C in the course of 1 hour. A solution is obtained, containing the not reacted epoxide resins of the formula V and the reaction product of the formula V with diethanolamine and gluconic acid, the reaction product corresponding to the epoxide resin of the formula I. The composition is to be best explained by the formula II.

The mixture was cooled to 40° C and 450 g of distilled water and 13.7 g of dicyandiamide were stirred in in the course of 1 hour. Finally, the solvent mixture was removed by azeotropic distillation with water in vacuo at 40° C. The resulting dispersion was filtered through a 56 μm gauze.

Characteristic values: Solids content: 65.8% Viscocity at 25° C : 1,984 mPas (Brookfield, Spindle 3/30 U) pH value : 3.7

The composition of the resin component of the dispersion is represented by formula II, wherein $R^1$ and $R^3$ have the same meaning as in formula II, $R^2$ and $R^4$ denote H, $R^5$ and $R^6$ denote the radical $-CH_2-CH_2-OH$, $A^\ominus$ denotes the radical $CH_2(OH)[CH(OH)]_4COO^\ominus$, n has a value from 9.7 to 13.0 and $n_1 : n_3$ has a value from 3.6 to 4.0.

11 g of the received dispersion were well stirred with 1.1% of tylose H 4,000, relative to solids content (hydroxy ethyl cellulose of Messrs. Hoechst AG, with a medium content of $OC_2H_4$ of 35%), further with 3 g of hexamethoxy methylmelamine (described by Messrs. Hoechst AG in technical leaflet as MF 900) and 1 g of 8.5% strength $H_3PO_4$. By means of this coating agent a film 24 μm thick was applied to electrolytic sheet metal by means of a Handcoater and was exposed to the air for 10 minutes and stoved for 10 minutes at 200° C. A glossy, transparent film of good elasticity and good resistance to sterilisation was obtained.

EXAMPLE 8

363.7 g of an epoxide resin of the general formula V wherein n has a value from 5.0 to 5.8, having a softening point of 95° C by the Durrans method and an epoxide equivalent weight of 910 (an epoxide resin of this type is described by Messrs. Hoechst AG under the designation EP 304 in the technical leaflets "Epoxidharze" ("Epoxide Resins")) were melted. 45 g of toluene and 135 g of n-butanol were added at 125° C to the melt in the course of 1 hour, and the temperature fell gradually to 80° C. 4 g (0.01 mol/100 g of EP resin) of diethanolamine were then added in the course of 15 minutes. The mixture was left to react further at 80° C for one hour and 11 g of 50% strength gluconic acid were then added to 70° C in the course of 1 hour. A solution is obtained, containing the not reacted epoxide resins of the formula V and the reaction product of the formula V with diethanolamine and gluconic acid, the reaction product corresponding to the epoxide resin of the formula I. The composition is to be best explained by the formula II. The mixture was cooled to 40° C and 450 g of distilled water and 13.7 g of dicyandiamide were stirred in in the course of 1 hour. Finally, the solvent mixture was removed by azeotropic distillation with water in vacuo at 40° C. The resulting dispersion was filtered through a 56 μm gauze.

Characteristic values: Solids content: 63.1% Viscosity at 25° C : 1,284 mPas (Brookfield, Spindle 3/30 U) pH value : 3.8

The composition of the resin component of the dispersion is represented by formula II, wherein $R^1$ and $R^3$ have the same meaning as in formuly II, $R^2$ and $R^4$ denote H, $R^5$ and $R^6$ denote the radical $-CH_2-CH_2-OH$, $A^\ominus$ denotes the radical $CH_2(OH)[CH(OH)]_4COO^\ominus$, n has a value from 5.0 to 5.8 and $n_1 : n_3$ has a value from 8.8 to 9.2

The received dispersion was one time standardized to a content of 25% of hexamethoxy methylmelamine (see Example 4) and mixed with 10% of a 8.5% strength $H_3PO_4$ (relative to solids content), then alternately adjusted together with a phenolic resin dispersion (manufactured according to DT-OS No. 2,330,849, Example 1 d) to give a phenolic resin content of 25% and mixed with 10% of 8.5% strength $H_3PO_4$. The obtained films showed a good resistance to sterilisation.

What is claimed is:

1. A process for the manufacture of an aqueous coating agent containing an aqueous dispersion of a mixture of epoxide resin as a binder and an epoxide resin curing agent which comprises reacting a mixture containing said epoxide resin and curing agent wherein the epoxide resin binder is an epoxide resin mixture of at least one epoxide resin selected from the group consisting of
   (a) epoxide resins of the formula I

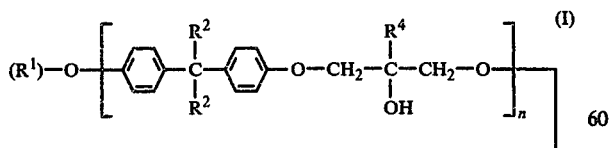

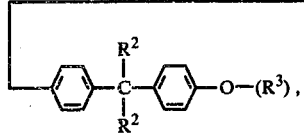

wherein $R^1$ denotes the radical

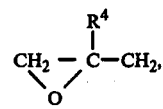

$R^2$ and $R^4$ denote H or $CH_3$ and $R^3$ denotes the radical

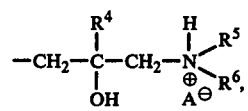

$A^\ominus$ representing the anionic radical of a monocarboxylic acid, and $R^5$ and $R^6$ having the following meanings:

| when $R^5$ is: | $R^6$ is: |
|---|---|
| H | $-CH_2CH_2OH$ |
| H | $-CH_2CH(OH)CH_3$ |
| $-CH_2CH_2OH$ | $-CH_2-CH_2OH$ |
| $-CH_2-CH(OH)CH_3$ | $-CH_2-CH(OH)CH_3$ | and n denotes values from 1.3 to 13; and solid epoxide resins of the formula V

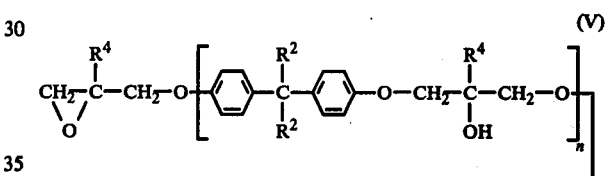

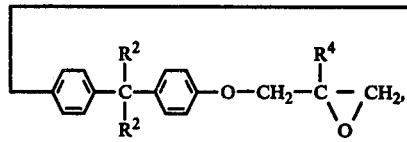

wherein $R^4$ and $R^2$ denote H or $CH_3$ and n has a value from 1.3 to 13, the resins having epoxide equivalent weights from 300 to 2,000 and the softening points by the Durrans method being between 50 and 125° C, the mixture of epoxide resins of the formula I and V having the condition that the obtained epoxide resin mixture a' of the formula II

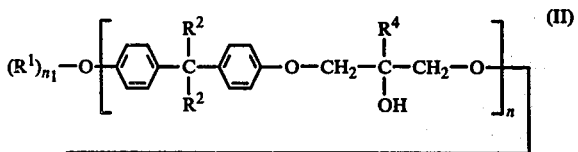

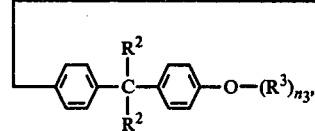

wherein $R^1$, $R^2$, $R^3 R^4$, $R^5$, n and $A\ominus$ have the meaning already mentioned and the sum of $n_1$ and $n_3$ has the value 2 and the ratio of $n_1:n_3$ has values from 20 to 0.1, preferably from 10 to 0.1, and (b) an epoxide resin mixture consisting of epoxide resins of the formula I'

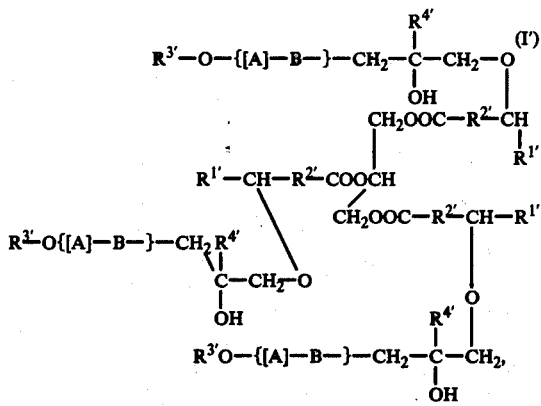

wherein A is the radical

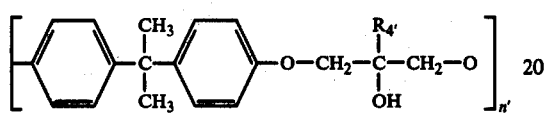

when B represents the radical

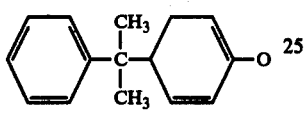

or A is the radical

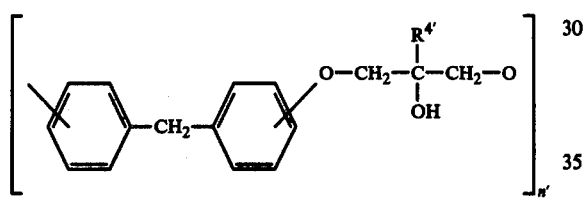

when B represents the radical 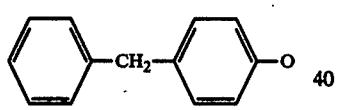

or A represents the radical 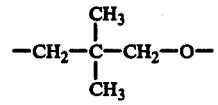
when B has the value zero, or A represents the radical 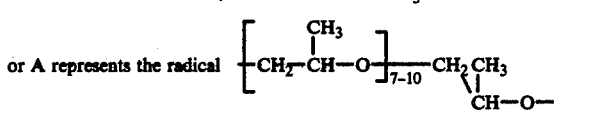

when B has the value zero, and $R^{1'}$ denotes the radical $-(CH_2)_5-CH_3-$ and $R^{2'}$ denotes the radical $-(CH_2)_7-CH=CH-CH_2-$, n' has the value 0 to $R^{3'}$ denotes the radical

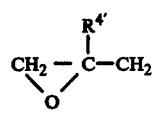

or the radical

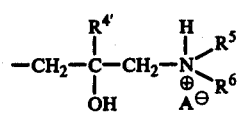

and wherein the last-mentioned grouping is present in at least one radical $R^{3'}$ and $R^5$ and $R^6$ have the following meanings:

| when $R^5$ is: | $R^6$ is: |
|---|---|
| H | $-CH_2CH_2OH$ |
| H | $-CH_2CH(OH)CH_3$ |
| $-CH_2CH_2OH$ | $-CH_2-CH_2OH$ |
| $-CH_2-CH(OH)CH_3$ | $-CH_2-CH(OH)CH_3$ | and $A\ominus$ represents the anionic radical of a monocarboxylic acid, and epoxide resins of the formula V'

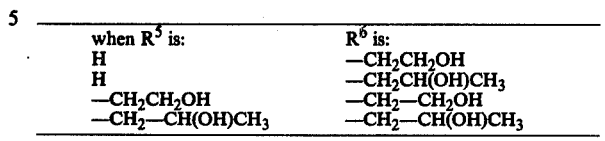

wherein $R^{3'}$ has the meaning

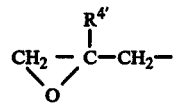

and $R^{1'}$, $R^{2'}$, $R^{4'}$, A, B and n' have the meaning already mentioned and the resins have epoxide equivlaent weights of approximately 440 to approximately 4,000, the mixture of epoxide resins of the formula I' and V' having the condition that the obtained apoxide resin mixture b' of the formula II'

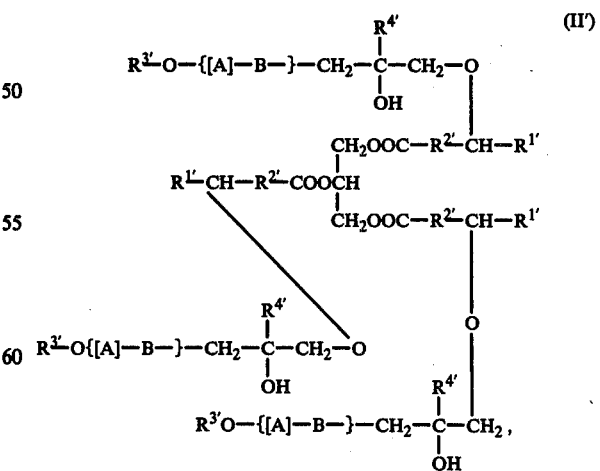

wherein $R^1$, $R^{2'}$, $R^{4'}$, $R^{5'}$, $R^{6'}$, A, B and $A\theta$ have the meaning already mentioned, wherein $R^{3'}$ denotes the radical

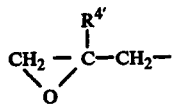

or the radical

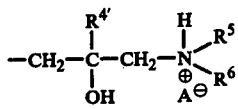

and the last-mentioned grouping is represented by a proportion of at least 10% and at most a proportion of 95%, at 50° to 100° C, while stirring, with 0.1 to 1.0 mol, relative to 100 g of the epoxide resin mixture, of an alkanolamine or dialkanolamine having the formula VI

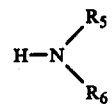
(VI)

wherein $R_5$ and $R_6$ have the meaning mentioned above, in the presence of at least one inert organic solvent selected from the group consisting of toluene, n-butanol and mixtures of toluene and n-butanol, and 0.01 to 1.0 mol of monocarboxylic acid, relative to 100 g, of epoxide resin mixture, having a pKa value of 2 to 5 is added to the resulting reaction product, it being necessary that the equivalent ratios of monocarboxylic acid to alkanolamine or dialkanolamine is 0.7:1 to 3:1, adding water to the resulting mixture while mixing vigorously at 20 to 70° C, and removing the organic solvent present in the mixture by azeotropic distillation thereof with water under vacuum pressure at 30° to 60° C.

2. An aqueous coating agent obtained by a process according to claim 1.

* * * * *

UNITED STATES PATENT AND TRADEMARK OFFICE
CERTIFICATE OF CORRECTION

PATENT NO. : 4,132,692

DATED : January 2, 1979

INVENTOR(S) : Görlitz et al.

It is certified that error appears in the above-identified patent and that said Letters Patent are hereby corrected as shown below:

Col. 1, line 23; "it," should read -- it is, --
Col. 2, line 38; "carboxlic" should read -- carboxylic --
Col. 3, line 34; "aquoeus" should read -- aqueous --
Col. 6, line 43; "misture" should read -- mixture --
Col. 7, lines 31 & 32; "diyandiamide" should read -- dicyandiamide --
Col. 7, line 32; "expoxide" should read -- epoxide --
Col. 8, line 26; "mentiond" should read -- mentioned --
Col. 8, line 63; "soltuion" should read -- solution --
Col. 8, line 67; "descirbed" should read -- described --
Col. 9, lines 14 & 15; "Heidelbert" should read -- Heidelberg --
Col. 9, line 47; "denots" should read -- denotes --
Col. 9, line 63; "und" should read -- and --
Col. 9, line 66; "Göttinger" should read -- Göttingen --
Col. 10, line 47; "eoxide" should read -- epoxide --
Col. 10, line 58; "eoxide" should read -- epoxide --
Col. 11, line 26; "descirbed" should read -- described --
Col. 11, line 44; "descirbed" should read -- described --
Col. 11, line 61; "sterlisation" should read -- sterilisation --

Col. 12, line 2; "expoide" should read -- epoxide --
Col. 12, line 22; "ehterification" should read -- etherification --
Col. 12, line 26; "70&" should read -- 70% --
Col. 12, line 28; "latic" should read -- lactic --

UNITED STATES PATENT AND TRADEMARK OFFICE
CERTIFICATE OF CORRECTION

PATENT NO. : 4,132,692
DATED : January 2, 1979
INVENTOR(S) : Görlitz et al.

It is certified that error appears in the above-identified patent and that said Letters Patent are hereby corrected as shown below:

Col. 12, line 42; "$\mu$" should read -- $\mu m$ --
Col. 12, line 45; "Spindel" should read -- Spindle --
Col. 12, line 54; "$COO\alpha$," should read -- $COO^\ominus$, --
Col. 13, line 6; "constitutent" should read -- constituent --
Col. 13, line 32; "techanical" should read -- technical --
Col. 13, line 57; "quantitiative" should read -- quantitative --
Col. 13, line 61; "axeotropic" should read -- azeotropic --
Col. 13, line 64; "mPas" should read -- Characteristic --
Col. 13, lines 67 & 68; "dipersion" should read -- dispersion --
Col. 14, line 8; "constituent," should read -- constituent --
Col. 15, line 50; "radical." should read -- radical --
Col. 16, line 21; "compositin" should read -- composition --
Col. 16, line 32; "R3" should read -- $R^3$ --
Col. 16, line 34; "-$CH_2$-$CH^2$-" should read -- -$CH_2$-$CH_2$- --
Col. 18, line 1; "$A^\ominus$ $CH_2$" should read -- $A^\ominus$ denotes the radical $CH_2$ --
Col. 18, line 2; "9.7 tl 13.0" should read -- 9.7 to 13.0 --
Col. 18, line 20; "1.865" should read -- 1,865 --
Col. 18, lines 43 & 44; "Viscocity" should read -- Viscosity --
Col. 19, line 30; "formuly" should read -- formula --
Col. 21, lines 53 & 54; "0 to $R^{3'}$" should read -- 0 to 13, preferably 0 to 6, $R^4$ denotes H or $CH_3$, $R^{3'}$ -- Response and Amendment dated June 16, 1978, page 4, second line from bottom.

UNITED STATES PATENT AND TRADEMARK OFFICE
CERTIFICATE OF CORRECTION

PATENT NO. : 4,132,692
DATED : January 2, 1979
INVENTOR(S) : Görlitz et al.

It is certified that error appears in the above-identified patent and that said Letters Patent are hereby corrected as shown below:

Col. 22, line 41; "equivlaent" should read -- equivalent -- Response and Amendment dated June 16, 1978, page 6, line 2.
Col. 22, line 44; "apoxide" should read -- epoxide -- Response and Amendment dated June 16, 1978, page 6, line 4.

Signed and Sealed this

Fifteenth Day of May 1979

[SEAL]

Attest:

RUTH C. MASON
Attesting Officer

DONALD W. BANNER
Commissioner of Patents and Trademarks